US005472405A

United States Patent [19]
Buchholtz et al.

[11] Patent Number: 5,472,405
[45] Date of Patent: Dec. 5, 1995

[54] THERAPY APPARATUS FOR THE TREATMENT OF PATHOLOGICAL TISSUE WITH A CATHETER

[75] Inventors: Gerhard Buchholtz; Ulrich Schaetzle, both of Erlangen, Germany

[73] Assignee: Siemens Aktiengesellschaft, Munich, Germany

[21] Appl. No.: 190,905

[22] Filed: Feb. 3, 1994

[30] Foreign Application Priority Data

Apr. 2, 1993 [DE] Germany .................. 43 10 924.1

[51] Int. Cl.$^6$ ..................................................... A61H 1/00
[52] U.S. Cl. ............................................. 601/2; 128/660.03
[58] Field of Search ................. 601/2, 4; 128/660.03, 128/662.03, 662.06

[56] References Cited

U.S. PATENT DOCUMENTS

| | | | |
|---|---|---|---|
| 4,889,122 | 12/1989 | Watmough et al. | 128/399 |
| 5,078,144 | 1/1992 | Sekino et al. | 128/660.03 |
| 5,158,536 | 10/1992 | Sekins et al. | 128/898 X |
| 5,161,536 | 11/1992 | Vilkomerson et al. | 128/660.07 |
| 5,178,481 | 1/1993 | Lacoste et al. | 128/660.03 |
| 5,188,111 | 2/1993 | Yates et al. | 128/662.06 X |
| 5,190,046 | 3/1993 | Shturman | 128/660.03 X |
| 5,213,571 | 5/1993 | Fujio et al. | 604/31 |
| 5,234,004 | 8/1993 | Hascoet et al. | 128/660.03 X |
| 5,269,292 | 12/1993 | Granz et al. | |
| 5,312,328 | 5/1994 | Nita et al. | 601/2 X |
| 5,357,805 | 10/1994 | Fujimoto et al. | 601/2 |

FOREIGN PATENT DOCUMENTS 0017646 9/1993 WIPO .................. 128/660.03

*Primary Examiner*—William E. Kamm
*Assistant Examiner*—Brian L. Casler
*Attorney, Agent, or Firm*—Hill, Steadman & Simpson

[57] ABSTRACT

A therapy apparatus for the treatment of pathological tissue with focused ultrasound waves, has a catheter introducible into the body of a living subject to be treated and having at least one pressure sensor disposed at the region of its distal end. A control unit to which the output signal of the pressure sensor is supplied generates an alarm signal if the level of the output signal of the pressure sensor exceeds a limit value, thereby minimizing the risk of damaging healthy tissue.

11 Claims, 3 Drawing Sheets

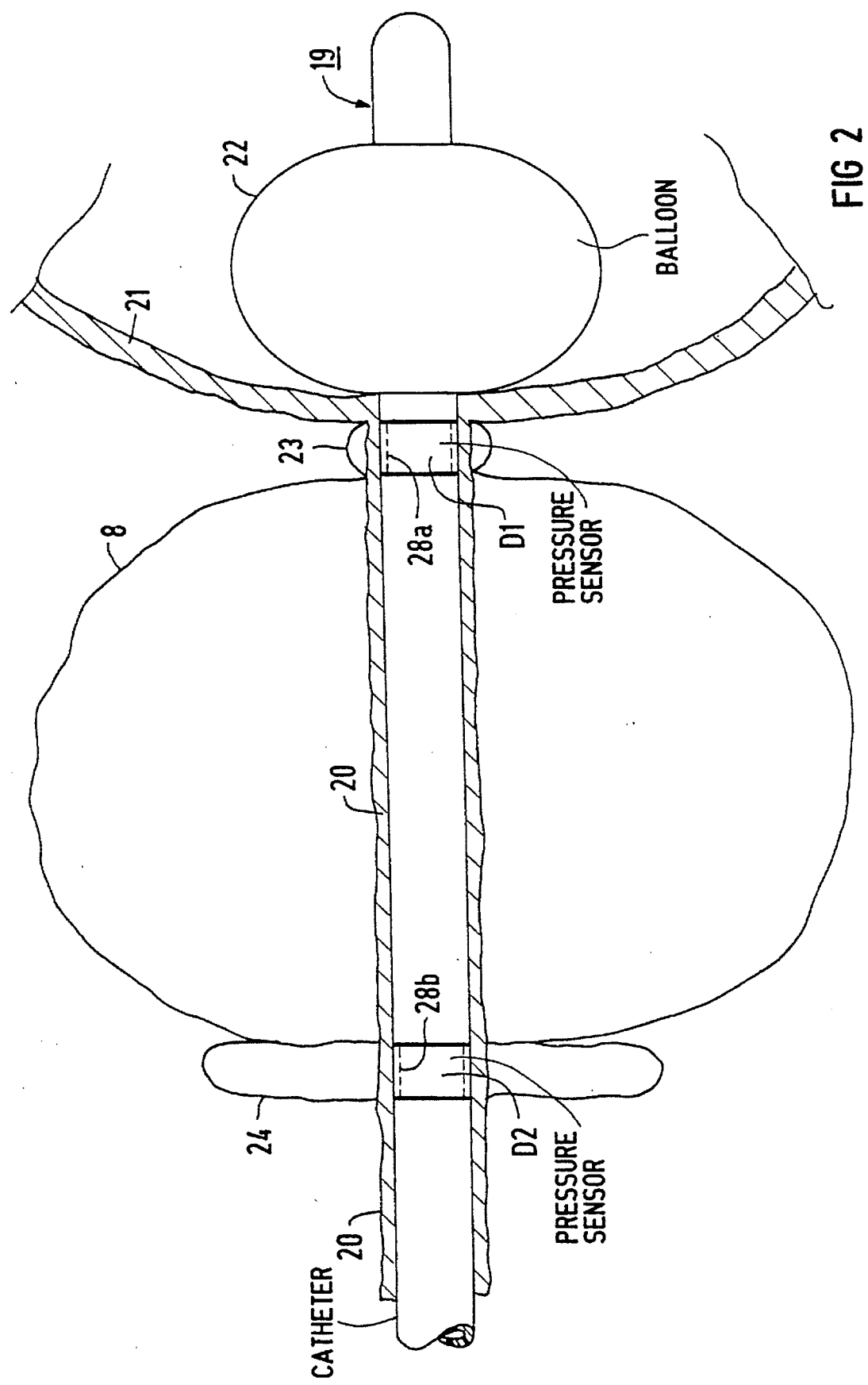

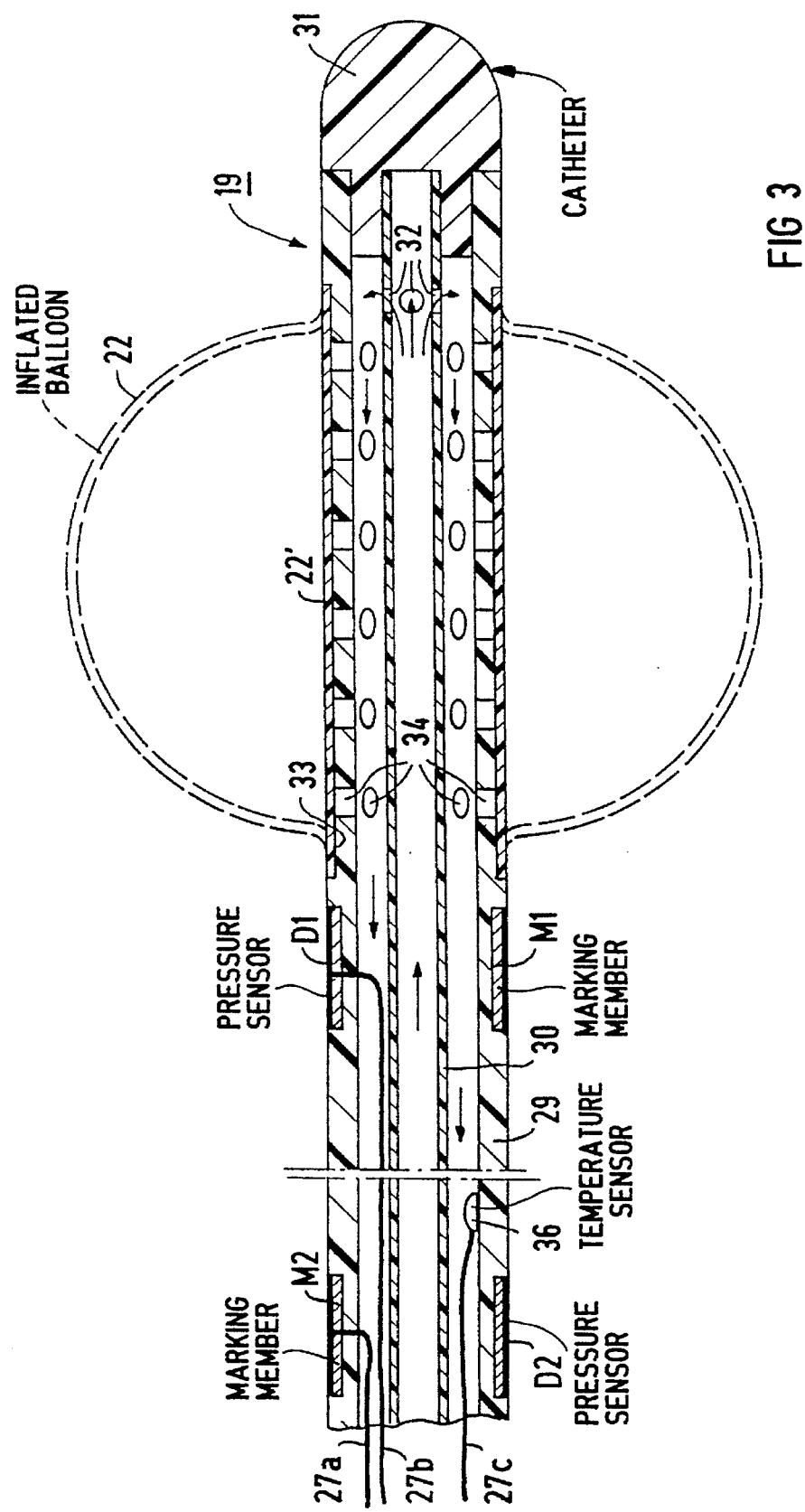

THERAPY APPARATUS FOR THE TREATMENT OF PATHOLOGICAL TISSUE WITH A CATHETER

BACKGROUND OF THE INVENTION

1. Field of the Invention

The present invention is directed to a therapy apparatus for the treatment of pathological tissue in a living subject on the basis of charging with heating radiation, whereby an ultrasound locating means for locating a region to be treated and a catheter introducible in the body of the life form, which serves the purpose of monitoring the therapy event, are provided.

2. Description of the Prior Art

In therapy apparatus, systems of the above type, the pathological tissue is heated by the heating radiation, for example microwaves or ultrasound waves. As far as the resulting temperatures lie below 45° C., the cell metabolism is disturbed, with the consequence that a retardation of the growth in the case of tumors, or even an abatement of the tumor occurs. This type of treatment is referred to as local hyperthermia. When temperatures beyond 45° C. are reached, the cell protein coagulates, with the result of necrotization of the tissue. This latter type of treatment is referred to as thermotherapy.

In order to avoid unintentional irradiation of healthy tissue in the case of local hyperthermia and the unintentional necrotization of healthy tissue in the case of thermotherapy, suitable measures must be undertaken. In this context, U.S. Pat. No. 4,889,122 discloses the arrangement of temperature sensors in the pathological tissue and in the environment thereof in order to be able to acquire the intensity distribution of the active ultrasound. It is also known to bring a catheter into the region of the pathological tissue in a suitable way and to monitor the resulting temperatures with a temperature sensor integrated into the catheter. Moreover, the catheter can have a coolant flowing through it in order to protect healthy tissue. Nonetheless, an unintentional irradiation or necrotization of healthy tissue cannot be reliably precluded. In particular, however, the necrotization of healthy tissue can lead to a severe injury to the patient. In the treatment, for example, of benign prostate hyperplasia (BPH), there is the risk of damage to one or both bladder sphincters. Damage to the sphincter externus leads to incontinence on the part of the patient; damage of the sphincter internus deteriorates the reproductive capability of the patient as a consequence of retrograde ejaculation.

SUMMARY OF THE INVENTION

It is an object of the present invention to provide a therapy apparatus of the type initially, generally described such that the risk of unintentional tissue damage, particularly necrotization of healthy tissue, is at least reduced.

This object is achieved in accordance with the principles of the present invention in a therapy apparatus for treating pathological tissue with focused ultrasound waves including a source of focused ultrasound waves, a catheter introducible into the body of the subject to be treated, the catheter being provided with at least one pressure sensor in the region of its distal end, and a control unit to which the output signal of the pressure sensor is supplied which emits an alarm signal and/or suppresses the output of ultrasound waves, or at least lowers the intensity of the ultrasound waves, when the level of the output signal of at least one pressure sensor exceeds a limit value.

Before the beginning of the treatment, the catheter is placed using diagnostic ultrasound monitoring such as an ultrasound locating means, such that the pressure sensor is located in the region of that tissue to which damage is to be precluded. The placement of the catheter can ensue either using natural paths or through a skin puncture or endoscopically. When the treatment is then begun, the level of the output signal of the pressure sensor will be higher the closer the focus zone of the focused ultrasound waves is located to the pressure sensor. When the focus zone of the ultrasound waves approaches the pressure sensor and thus the tissue to be protected, to such an extent that the level of the output signal of the pressure sensor exceeds the limit value, an alarm signal is triggered which informs the operating personnel that further approach of the focus zone to the tissue to be protected is dangerous or must be suppressed. Alternatively, or additionally, the output of ultrasound waves is entirely suppressed or at least lowered to such an extent that the level of the output signal of the pressure sensor drops below the limit value.

Thus in the case of the therapy apparatus of the invention that the risk of unintentional tissue damage, particularly necrotization of tissue is noticeably reduced, if not precluded. If as the therapy apparatus contains an ultrasound locating means which produces ultrasound images of the tissue zone to be treated, there is also the possibility of electronically acquiring the position of the pressure sensor in the ultrasound image. This is easily possible by identifying the point in time of the appearance of that output signal of the pressure sensor which arises when the tissue region to be treated is charged with diagnostic ultrasound for producing an ultrasound image. A defined location in the resulting ultrasound image corresponds to this point in time. When, moreover, the spatial position of the ultrasound applicator used for generating the ultrasound images is known— this, for example, can be acquired with the assistance of distance sensors—, then the spatial position of the pressure sensor can be calculated. It is then possible without further difficulty to control the movement of the source of the ultrasound waves and the body of the patient relative to one another, such that the risk of charging the tissue zone to be protected is avoided from the very outset under normal conditions.

A further object of specifying a therapy apparatus particularly suited for treating prostate conditions, for example benign prostate hyperplasia or prostate carcinoma, is achieved in an embodiment wherein the catheter is adapted for introduction into the urethra and is provided with two pressure sensors which are arranged spaced from one another along the catheter, the spacing between the sensors corresponding to the spacing between the sphincter externus and sphincter internus of the patient to be treated. Injury to the sphincters can thus be easily avoided because too close an approach of the focus zone of the ultrasound waves to one of the sphincters leads to an upward transgression of the limit value by the output signal of the corresponding pressure sensor. The spacing between the two sphincters can be easily calculated from the ultrasound image in a known way; the suitable catheter is then selected from a plurality of catheters kept on hand, each thereof having a different spacing between the marking members (pressure sensors), whereby the spacing, for example, can be graduated from catheter-to-catheter in steps of two millimeters each.

In order to facilitate the positioning of the catheter, one version of the invention includes an expandable balloon at the distal end of the catheter, this expandable balloon having a spacing from the pressure sensor neighboring it which is equal to the average spacing of the inside of the urinary bladder from the sphincter internus. In the catheterization, one then proceeds such that the catheter—with an unexpanded balloon— is initially introduced to such an extent that it is located within the urinary bladder. Subsequently, the balloon is expanded and the catheter is retracted to such an extent that the side of the balloon facing away from the distal end of the catheter is seated against the inside wall of the urinary bladder. The pressure sensor neighboring the distal end of the catheter is then located inside the sphincter internus, whereas the other pressure sensor is located within the sphincter externus, given a properly selected spacing of the pressure sensor from one another. The positioning of the catheter can be easily monitored in the ultrasound image as warranted.

In a further version of the invention, the catheter is provided with an acoustic marking member at least one pressure sensor, the acoustic impedance of the marking member thereof deviating from that of the surrounding tissue. As a result of this measure, first, the positioning of the catheter under ultrasound monitoring is facilitated, since the marking member is clearly recognizable in the ultrasound image due to its acoustic impedance which differs from that of the surrounding tissue, so that it is easily possible to find that alignment of the catheter wherein the pressure sensor is located at the desired location. Second, an additional, optical marking of the tissue region to be protected against damage ensues in the ultrasound image, so that the risk that such damage nonetheless occur is again reduced.

In another embodiment of the invention the catheter has means for circulating a coolant through the catheter during operation, so that injury to healthy tissue adjoining the catheter is practically precluded in the case of benign prostate hyperplasia of the urethra.

In a further embodiment of the invention the catheter is provided with at least one temperature sensor in the region of its distal end, potentially between the two pressure sensors, so that a qualitative acquisition of the temperature present in the tissue to be treated is possible.

DESCRIPTION OF THE DRAWINGS

FIG. 2 is an enlarged, schematic illustration of the distal end of the catheter of FIG. 1 introduced into the body of the patient, together with the surrounding organs.

FIG. 3 is a longitudinal section through the distal end of a further embodiment of the catheter of the invention.

DESCRIPTION OF THE PREFERRED EMBODIMENTS

Figure 1:
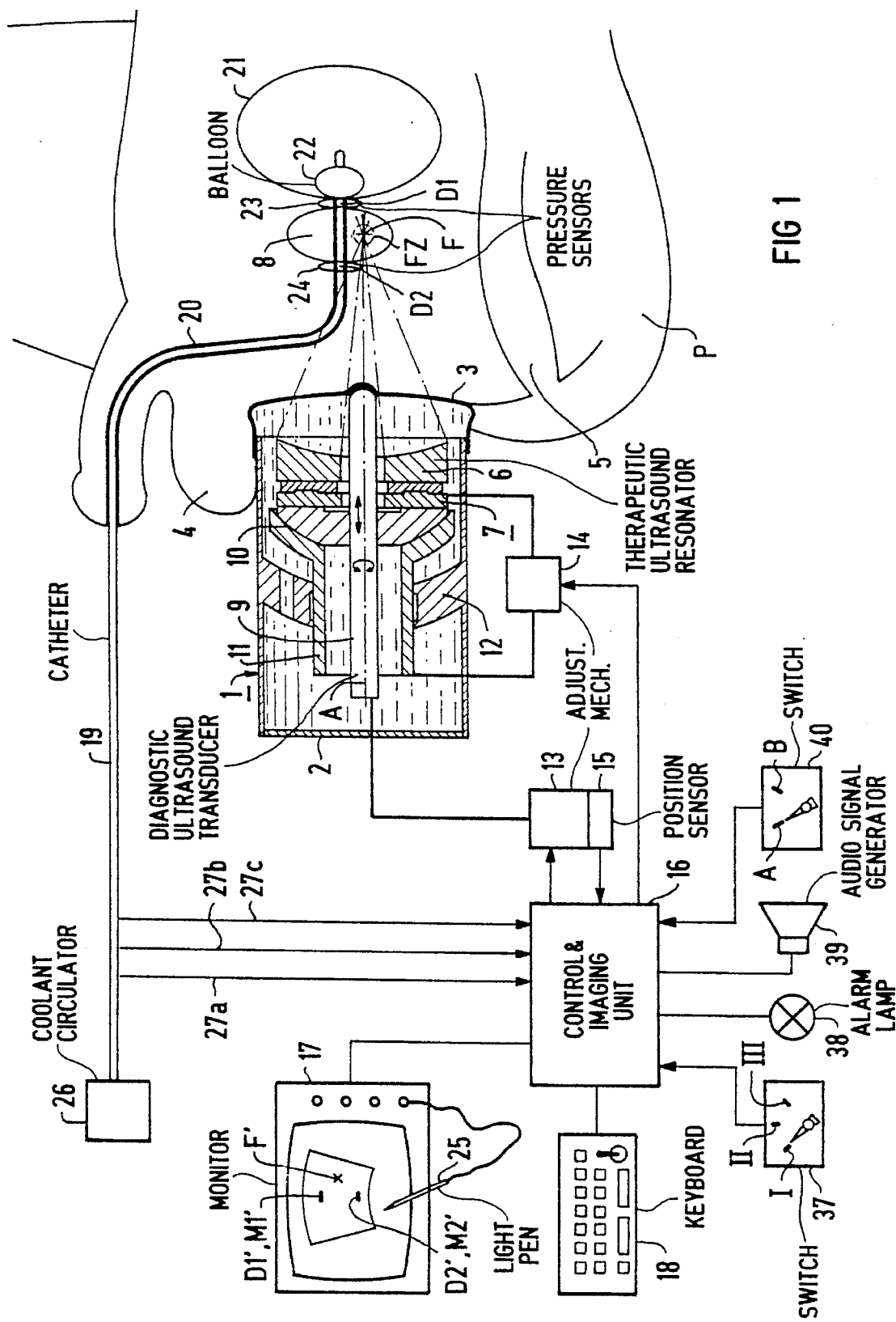
FIG. 1 is a schematic illustration of a longitudinal section through the body of a patient and a therapy apparatus of the invention applied thereto and an introduced catheter.

FIG. 1 shows an apparatus for the treatment of benign prostate hyperplasia that, among other things, includes a therapeutic ultrasound applicator 1 as a source of focused therapeutic ultrasound waves. This has a housing 2 filled with a liquid acoustic propagation medium, for example water, and that has an application end closed with a flexible coupling membrane 3. This serves the purpose of coupling the ultrasound applicator 1 to the patient surface of a body P for acoustic coupling, namely in the region of the perineum, i.e. between scrotum 4 and rectum 5 of the patient P. For acoustic coupling, the coupling membrane 3 of the ultrasound applicator 1 is pressed against the body surface of the patient P.

An ultrasound resonator 6 for generating therapeutic ultrasound, whose emission face has a concave, spherically curved shape, is located in the inside of the housing 2. The ultrasound resonator 6 is attached on a carrying member composed of a plurality of parts generally referenced 7. The ultrasound resonator 6 is constructed in a known way, i.e. the ultrasound resonator 6 can be a single, appropriately shaped piezoceramic member; the ultrasound transducer 6, however, may alternatively be composed mosaic-like from a plurality of small piezoceramic transducers. In both instances, a backing or carrying member (not shown) having a suitable thickness that is formed of a material having a suitable acoustic impedance can be provided in a known way.

The ultrasound resonator 6 has an acoustic axis A along which the generated ultrasound waves propagate, these waves converging in a focus F which is at the center of the spherically curved emission face of the ultrasound resonator 6. The focus F is surrounded by a focus zone FZ that is indicated with broken lines in FIG. 1. The focus zone FZ means that zone within which the peak pressure of the ultrasound waves is not lower than half the peak pressure maximally occurring in the focus zone FZ (−6 dB zone). The drive of the ultrasound transducer 6 ensues with an electrical generator contained in a control and imaging unit described below.

A diagnostic ultrasound locating transducer 9, preferably a B-scan applicator which is a component of an ultrasound locating means that serves the purpose of locating the region to be treated, i.e. the prostate 8, is accepted in a bore of the carrier member 7. In order to be able to align the ultrasound locating transducer 9 relative to the prostate 8 such that a good image is achieved, the ultrasound locating transducer 9 is accepted longitudinally displaceable and rotatable in the bore of the carrier member 7, as indicated in FIG. 1 with appropriate arrows. During operation of the ultrasound locating transducer 9, it is pressed against the body surface of the patient P with the coupling membrane 3 interposed therebetween in order to obtain a good image quality.

As may be seen from FIG. 1, the carrier member 7 has a spherically curved bearing surface 10 at its side facing away from the ultrasound transducer, this bearing surface 10 interacting with a spherical cap-shaped bearing surface having a corresponding radius of a bearing member 11 that is accepted longitudinally displaceable but non-rotatable in the bore of a housing flange 12. The center of the bearing surface 10 differs from the focus F. It is thus possible to spatially modify the alignment of the ultrasound resonator 6 and of the ultrasound locating transducer 9 relative to the body of the patient P without the occurrence of a relative motion between the coupling membrane 3 and the body surface of the patient P.

An adjustment mechanism is provided for adjusting the ultrasound locating transducer 9 relative to the carrier member 7. An adjustment mechanism 14 is provided for displacement of the ultrasound resonator 6 relative to the carrier member 7 as well as for displacement of the carrier member 7 with the ultrasound resonator 6 relative to the housing 2 and to the coupling membrane 3, and thus relative to the region to be treated, namely the prostate 8. The adjustment mechanisms 13 and 14, that are schematically indicated in FIG. 1, are preferably motor-driven adjustment means. Means are allocated to the adjustment mechanism 13 for identifying the position of the ultrasound locating transducer 9 relative to the carrier member 7 and thus relative to the ultrasound applicator 1. Such means may be a position sensor 15 as schematically indicated in FIG. 1, which outputs signals corresponding to the momentary position of the ultrasound locating transducer 9 relative to the carrier member 7. Both adjustment mechanisms 13 and 14 as well as the position sensor 15 are connected to a control and imaging unit 16 to which a monitor 17 and a keyboard 18 are also connected. The control and imaging unit 16, includes image generating means such as ultrasound image processing circuitry, which interacts with the ultrasound locating transducer 9 in a known way to generate an ultrasound B-image that is displayed on the monitor 17. The arrangement of the ultrasound locating transducer 9 relative to the ultrasound resonator 6 is selected such that the acoustic axis A of the ultrasound resonator 6 lies in the body slice of the patient P shown in the ultrasound B-image. Taking the output signal of the position sensor 15 in the ultrasound image into consideration, the control and imaging unit 16 mixes a mark F' in that identifies the center of the focus zone FZ.

In addition to containing the imaging electronics required for producing ultrasound images, the control and imaging unit 16 contains all circuits, etc., that are required for driving the adjustment mechanisms 13 and 14, for driving the ultrasound resonator 6, as well as for evaluating the output signals of two pressure sensors D1 and D2. Further, the therapy apparatus includes a catheter 19 that is introduced into the urethra 20 of the patient P for the implementation of a treatment such that the distal end of the catheter 19 projects into the urinary bladder 21. The catheter 19 has an expandable balloon 22 disposed at the distal end of the catheter 19. The balloon 22 is inflated when the distal end of the catheter 19 is advanced into the urinary bladder 21. Subsequently, the catheter is retracted such that the balloon 22 presses against the region of the inside wall of the urinary bladder 21 surrounding the outlet of the urethra 21. The region of its distal end of the catheter 19, namely between the balloon 22 and the proximal end, is provided with the two aforementioned, acoustic pressure sensors D1 and D2. The pressure sensors D1 and D2 have a spacing from one another that essentially corresponds to the spacing between the sphincter internus 23 and sphincter externus 24 of the patient P to be treated, whereby the pressure sensor D1 has a spacing from that side of the balloon 22 facing toward it which corresponds to the average spacing of the inside of the urinary bladder 21 from the sphincter internus. As used herein, "average" means averaged over the patient population. The pressure sensors D1 and D2 are preferably annularly fashioned and are constructed using piezoelectrically activated polymer foil, for example polyvinylidene fluoride (PVDF) foil that is metallized in a known way for the formation of electrodes serving the purpose of electrical contacting.

The output signals of the pressure sensors D1 and D2 are supplied to the control and imaging unit 16 via respective lines 27a and 27b. The control and imaging unit 16 includes means for comparing at least those output signals of the pressure sensors D1 and D2 that arise due to ultrasound waves emanating from the ultrasound resonator 6 being incident on the pressure sensors D 1 and D2 during the treatment with a limit value. The limit value is dimensioned such that injury to the bladder sphincters is precluded as long as the amplitude of the ultrasound waves present in the region of the pressure sensors D1 and D2 is not so high that the output signal of the pressure sensors exceeds the limit value. The control and imaging unit 6 institutes remedial action in response to an upward transgression of the limit value dependent on which of three possible operating modes is selected with the switch 37.

In the operating mode corresponding to the switch position referenced I, the control and imaging unit 16 drives an alarm lamp 38 and/or an audio signal generator 39. Alternatively or additionally, there is the possibility of using the monitor 17 to provide an optical alarm signal, for example by causing the monitor image to flash when the limit value is exceeded.

In the operating mode corresponding to the switch position referenced II, the amplitude of the generated ultrasound waves is reduced to such an extent given an upward transgression of the limit value that the output signal of the pressure sensors D1 and D2 drops below the limit value.

In the operating mode corresponding to switch position III, the control and imaging unit 16 entirely suppresses the output of ultrasound waves given an upward transgression of the limit value.

In operating mode II as well as in operating III, the output of alarm signals can additionally ensue in the way set forth in conjunction with operating mode I.

In addition to the switch 37, a switch 40 is connected to the control and imaging unit 16, this switch 40 having two switch positions referenced A and B. When the switch 40 assumes switch position A, the control and imaging unit 16 evaluates the output signals of the pressure sensors D1 and D2 not only during operation of the ultrasound resonator 6 but also during the operation of the ultrasound locating transducer 9. The control and imaging unit 16 calculates the points in time at which those output signals of the pressure sensors D1 and D2 appear that arise due to the diagnostic ultrasound generated by the ultrasound locating transducer 9 being incident on the pressure sensors D1 and D2. A defined picture element or a defined image zone in the current ultrasound image corresponds to these points in time. Marks referenced D1' and D2' in FIG. 1 are mixed into the ultrasound image displayed on the monitor 17 at the corresponding locations. Utilizing the signal of the position sensor 15, the control and imaging unit 16 also calculates the position of the pressure sensors D1 and D2 relative to the focus zone FZ. When, by contrast, the switch 40 assumes its position referenced B, the consideration of the output signals of the pressure sensors D1 and D2 ensues only during operation of the ultrasound resonator 6 but not during operation of the ultrasound locating transducer 9.

For implementing a treatment, one proceeds by applying the coupling membrane 3 of the ultrasound applicator I to the perineum of the patient P to be treated—who preferably assumes what is referred to as the lithotomy position (see Pschyrembel, "Klinisches Woerterbuch", 185, $250^{th}$ Edition, page 1156)—so that no air bubbles are enclosed between the body surface and the coupling membrane 3. Following thereupon, the generation of ultrasound images is started by an appropriate actuation of the keyboard 18. Likewise by an appropriate actuation of the keyboard 18, the adjustment mechanisms 13 and 14 are now actuated such that an alignment of the ultrasound locating transducer 9 relative to the body of the patient P is obtained wherein the prostate 8 is imaged well in the ultrasound image. In a known way, for example by marking the sphincter internus 23 and the sphincter externus 24 in the ultrasound image with a light pen 25 or a similar input means, the distance of the two sphincters from one another is now determined by the control and imaging unit 16 and is displayed on the monitor 17. Subsequently, a catheter 19 is selected from a set of catheters 19, whose respective pressure sensors D1 and D2 have different spacings from one another, the pressure sensors D1 and D2 of the selected catheter 19 having a spacing from one another that essentially corresponds to the measured spacing between the two bladder sphincters of the patient P to be treated. Under diagnostic ultrasound monitoring, this catheter 19 is now introduced into the urethra 20 of the patient P and is positioned with the assistance of the balloon 22 such that the pressure sensors D1 and D2 are respectively located within the sphincter internus 23 or the sphincter externus 24. The proper positioning of the catheter 19 in the urethra 20 can be easily checked with reference to the marks D1' and D2' mixed into the ultrasound image when the switch 40 assumes its position A.

A region of the prostate 8 to be treated can now be marked with the light pen 25. In response to an appropriate actuation of the keyboard 18, the control and imaging unit 16 now actuates the adjustment mechanism 14 such that the focus zone F is displaced into that region of the prostate 8 that corresponds to the region in the ultrasound image marked with the light pen 25. This is shown in the ultrasound image in that the mark F' coincides with the region marked with the light pen 25 after the actuation of the adjustment mechanism 14 has ensued. When this is the case, the control and imaging unit 19 drives the ultrasound resonator 6 to generate therapeutic ultrasound. The therapeutic ultrasound is continuous sound that is administered over a chronological duration selected such that the temperature required for the necrotization of tissue—which usually lies beyond 45° C.—is exceeded. Following thereupon, a further region of the prostate 8 to be treated can again be marked with the light pen 25 and can be treated in the described way.

The risk that the sphincter internus 23 or sphincter externus 24 will be damaged or destroyed in this procedure, resulting in a degradation of the reproductive capability or in incontinence, is extremely slight since either the operating personnel are warned due to the evaluation of the output signals of the pressure sensors D1 and D2 in the above-described way (operating mode I), or the amplitude of the ultrasound waves is lowered to non-hazardous values (operating mode II) or the emission of ultrasound waves is completely suppressed (operating mode III) as soon as the intensity of the ultrasound waves in the region of the pressure sensors D1 and D2 and thus in the region of the bladder sphincters, upwardly exceeds the permissible limit value. A lowering of this risk is also achieved because the position of the two bladder sphincters is clearly identified by the marks D1' and D2' clearly visible in the ultrasound image when the switch 40 assumes position A, so that it is practically impossible to mistakenly mark a region to be treated with the light pen 25 which lies entirely or partially within one of the sphincters.

There is also the possibility, moreover, of tracing the contours of a region of the prostate 9 to be treated with the light pen 25 in the ultrasound image. In response to an appropriate actuation of the keyboard 18, the focus zone FZ is then displaced step-by-step within the region traced with the light pen 25 and upon activation of the ultrasound resonator 6 such that the entire, traced region is charged with ultrasound waves and is necrotized. As a consequence of the marks D1' and D2', the risk that a region to be treated is marked with the light pen 25 that mistakenly entirely or partially contains one or both bladder sphincters is inconceivably slight. Even if this were to mistakenly occur or if the switch 40 assumes its position referenced B wherein a mixing-in of the marks D1' and D2' does not ensue, injury would be precluded since either the operating personnel would be warned, or the amplitude of the ultrasound waves would be lowered, or the output of ultrasound waves would be suppressed dependent on whether the switch 37 is located in position I, II or III.

In that case wherein the control and imaging unit 16 calculates the positions of the pressure sensors D1 and D2 relative to the focus zone FZ in the way set forth, injury to the bladder sphincters can be precluded with even greater reliability in that the control and imaging unit 16—regardless of the marking of a region to be treated undertaken with the light pen 25—is not permitted, by suitable programming, to actuate the adjustment mechanism 14 in such a way that would lead to a displacement of the focus zone FZ into the current position of either pressure sensor D1 or D2.

In order also to preclude injury to the urethra 20, it is provided that a coolant flows through the catheter 19. For this purpose, a coolant circulator 26 is provided, which may also include means for dissipating heat from the coolant, and/or means for cooling the coolant. In order to be able to monitor the therapy process, temperature sensor is arranged in the region of the distal end of the catheter 19 between the pressure sensors D1 and D2. The signal supplied by this at least one temperature sensor is supplied to the control and imaging unit 16, as illustrated in FIG. 1 by a schematically indicated line 27c. Further details regarding the cooling and the arrangement of the sensors shall be set forth in conjunction with the catheter of FIG. 3.

The distal end of the catheter 19 correctly placed in the urethra 20 is shown in FIG. 2, wherein only the urethra 20 and the prostate 8 are shaded, for clarity. It can be seen a catheter 19 optimally corresponding to the anatomy of the patient P to be treated is used, since the spacing of the pressure sensors D1 and D2 from one another is identical to the spacing between sphincter internus 23 and sphincter externus. The annular pressure sensors D1 and D2, moreover, are accepted in grooves 28a and 28b.

The structure of a version of the catheter 19 in the region of its distal end may be seen in detail in FIG. 3. The catheter 19 is a double-lumen. Consequently, it has flexible, outer catheter tube 29 in which a likewise flexible, inner catheter tube 30 is coaxially arranged. A closure part 31 forming a round-off introduction end is provided at the distal end, this closure part 31 closing the outer catheter tube 29 liquid-tight. The inner catheter tube 30 is accepted liquid-tight in a bore of the closure part 31. Shortly before the closure part 31, the inner catheter tube 30 has a plurality of overflow openings 32 which produce a connection between the inner lumen surrounded by the inner catheter tube 30 and the outer lumen situated between the outer catheter tube 29 and the inner catheter tube 30. There is thus the possibility of having a preferably liquid coolant flow through the catheter 19 with the coolant circulator 26 in the way indicated by arrows in FIG. 3.

The catheter 19 of FIG. 3 differs from that of FIGS. 1 and 2 in that the pressure sensors D1 and D2 are not accepted directly into the grooves 28a and 28b of the outer catheter tube 29, but are attached on annular, acoustic marking members M1 and M2 which are respectively accepted into the grooves 28a and 28b of the outer catheter tube 29 together with the pressure sensors D1 and D2. The marking members M1 and M2 are composed of a material, for example stainless steel, whose acoustic impedance deviates from that of the surrounding tissue. The marking members M1 and M2 are thus clearly visible in the ultrasound images produced with the ultrasound locating transducer 9 and the control and imaging unit 16. The images M1' and M2' of the marking members M1 and M2 appear in the ultrasound image at the same location as the marks D1' and D2', for which reason the reference characters M1' and M2' are additionally shown in FIG. 1. When the acoustic marking members M1 and M2 of FIG. 3 are present, the monitoring of the output signals of the pressure sensors D1 and D2 during operation of the ultrasound locating transducer 9 can be foregone, since the positions of the pressure sensors D1 and D2 in the ultrasound image are indicated by the images M1' and M2' of the marking members M1 and M2. The position of the marking members M1 and M2 relative to the focus zone FZ can also be calculated with the control and imaging unit 16 on the basis of known methods of image processing and taking the output signal of the distance sensor 15 proceeding from the positions of the images M1' and M2', in the respective ultrasound image into consideration.

A channel 33 that accepts a flexible balloon part 22' is introduced into the outer surface of the outer catheter tube 29 between the closure part 31 and the pressure sensor D1. This balloon part 22' has the region of its two ends connected liquid-tight to the outer catheter tube 29, for example by gluing. As long as the pressure of the coolant flowing through the catheter 19 does not exceed a limit value, the balloon part 22' has its shape shown with solid lines in FIG. 3 wherein it lies against the bottom of the channel 33. Since a plurality of openings 34 penetrating the wall of the outer catheter tube 29 is provided in the region of the channel 33, however, there is the possibility of expanding the balloon part 22' to form the balloon 22 in the way indicated with broken lines in FIG. 3 by increasing the pressure of the coolant.

A temperature sensor 36 that is in communication with the control and imaging unit 16 via the schematically line 27c is applied to the inside wall of the outer catheter tube 29 at that side of the marking member M1 facing away from the balloon 22.

For example, silicon rubber or polyethylene (PE) are suitable as material for the outer catheter tube 29, for the inner catheter tube 30 and for the closure part 31.

The exemplary embodiment set forth above is directed to the treatment of benign prostate hyperplasia, however, other conditions can also be treated. If tumors are to be treated, it can be provided that the regions to be treated are only heated to such an extent that a disruption of the cell metabolism occurs, but coagulation of the cell protein is not caused.

In the case of the exemplary embodiments set forth above, the output signals of the pressure sensors D1 and D2 are monitored during the operation of the ultrasound resonator 6 as well as during the operation of the ultrasound locating transducer 9. Unintentional injury to the bladder sphincters can thereby be avoided with especially high reliability. As a rule, however, it will usually suffice to undertake a monitoring of the output signals of the pressure sensors D1 and D2 either only during operation of the ultrasound resonator 6 or only during operation of the ultrasound locating transducer 9. Clearly the desired therapeutic effect need not necessarily be achieved using ultrasound waves in that case wherein an evaluation of the output signals of the pressure sensors D1 and D2 ensues only during operation of the ultrasound locating transducer 9. Other types of heating radiation, for example microwaves, can then alternatively be employed.

The generation of the ultrasound waves need not necessarily ensue using a piezoelectric ultrasound resonator. There is also the possibility of employing ultrasound transducers that operate according to other principles, for example magnetostrictively. Further, the focusing of the ultrasound waves need not necessarily ensue on the basis of a corresponding shaping of the emission face of the ultrasound resonator. Acoustic lenses and/or reflectors can also be employed for focusing.

Although modifications and changes may be suggested by those skilled in the art, it is the intention of the inventors to embody within the patent warranted hereon all changes and modifications as reasonably and properly come within the scope of their contribution to the art.

We claim as our invention:

1. A therapy apparatus for treating pathological tissue with therapeutic ultrasound, comprising:

a therapeutic ultrasound source which emits therapeutic ultrasound and including means for focusing said therapeutic ultrasound at pathological tissue to be treated in the body of a subject;

a catheter introducible into the body of said subject, said catheter having a distal end locatable in a region of said pathological tissue, said catheter carrying a pressure sensor at said distal end, said pressure sensor generating an output signal indicative of pressure present at said distal end of said catheter arising due to said therapeutic ultrasound emitted by said therapeutic ultrasound source; and control means, connected to said pressure sensor and supplied with said output signal of said pressure sensor, for instituting remedial action if a level of said output signal arising due to said therapeutic ultrasound emitted by said therapeutic ultrasound source exceeds a predetermined value.

2. A therapy apparatus as claimed in claim 1 wherein said control means comprises means for generating an alarm signal when said level of said output signal exceeds said predetermined value.

3. A therapy apparatus as claimed in claim 1 wherein said control means comprises means for suppressing delivery of said therapeutic ultrasound from said source of therapeutic ultrasound when said level of said output signal exceeds said predetermined value.

4. A therapy apparatus as claimed in claim 1 wherein said therapeutic ultrasound has an intensity, and wherein said control means comprises means for lowering said intensity of said therapeutic ultrasound if said level of said output signal exceeds said predetermined value.

5. A therapy apparatus as claimed in claim 1 for use in treating prostate conditions, and wherein said catheter is adapted for introduction into the urethra of said subject, said catheter carrying a further pressure sensor, spaced from said pressure sensor along said catheter, at a distance corresponding to a spacing between the sphincter externus and sphincter internus of said subject.

6. A therapy apparatus as claimed in claim 1 further comprising:

an expandable balloon carried on said catheter at said distal end, said expandable balloon being spaced along said catheter from said pressure sensor by a distance equal to an average distance of a patient population between the inside of the urinary bladder and the sphincter internus of said subject.

7. A therapy apparatus as claimed in claim 1 further comprising:

means connected to said control means for generating an ultrasound image of said region of said subject; and an acoustic marking member carried on said catheter at a location substantially coinciding with said pressure sensor, said acoustic marking member having an acoustic impedance deviating from the acoustic impedance of tissue in said region so that said marking member is visible in the ultrasound image generated by said means for generating an ultrasound image.

8. A therapy apparatus as claimed in claim 1 further comprising means for circulating a coolant through said catheter.

9. A therapy apparatus as claimed in claim 1 further comprising:

a temperature sensor carried by said catheter at said distal end.

10. A therapy apparatus as claimed in claim 9, further comprising a further pressure sensor carried on said catheter spaced a distance along said catheter from said pressure sensor, and wherein said temperature sensor is disposed on said catheter between said pressure sensor and said further pressure sensor.

11. A therapy apparatus for treating pathological tissue with focused therapeutic ultrasound, comprising:

a therapeutic ultrasound source for generating and emitting therapeutic ultrasound;

a catheter introducible into the body of said subject, said catheter having a distal end locatable in a region of said pathological tissue, said catheter carrying a pressure sensor at said distal end, said pressure sensor generating an output signal indicative of pressure present at said distal end of said catheter arising due to said therapeutic ultrasound emitted by said therapeutic ultrasound source; and control means, connected to said pressure sensor and supplied with said output signal of said pressure sensor, for instituting remedial action if a level of said output signal arising due to said therapeutic ultrasound emitted by said therapeutic ultrasound source exceeds a predetermined level.

\* \* \* \* \*